US006550917B1

(12) United States Patent
Neal et al.

(10) Patent No.: US 6,550,917 B1
(45) Date of Patent: Apr. 22, 2003

(54) DYNAMIC RANGE EXTENSION TECHNIQUES FOR A WAVEFRONT SENSOR INCLUDING USE IN OPHTHALMIC MEASUREMENT

(75) Inventors: Daniel R. Neal, Tijeras, NM (US); Darrell J. Armstrong, Albuquerque, NM (US); Daniel M. Topa, Albuquerque, NM (US); Richard J. Copland, Albuquerque, NM (US)

(73) Assignee: WaveFront Sciences, Inc., Albuquerque, NM (US)

( * ) Notice: Subject to any disclaimer, the term of this patent is extended or adjusted under 35 U.S.C. 154(b) by 102 days.

(21) Appl. No.: 09/692,483

(22) Filed: Oct. 20, 2000

Related U.S. Application Data

(60) Provisional application No. 60/182,088, filed on Feb. 11, 2000.

(51) Int. Cl.[7] .................................................. A61B 3/10
(52) U.S. Cl. ..................................................... 351/221
(58) Field of Search ................................ 351/158, 200, 351/205, 208, 211, 212, 213, 215, 216, 221, 246, 207; 250/201.9; 356/138, 392

(56) References Cited

U.S. PATENT DOCUMENTS

| | | | |
|---|---|---|---|
| 3,819,256 A | | 6/1974 | Bellows et al. |
| 4,021,102 A | | 5/1977 | Iizuka |
| 4,471,447 A | * | 9/1984 | Williams et al. ............. 364/525 |
| 4,678,297 A | * | 7/1987 | Ishikawa et al. ............ 351/208 |
| 4,725,138 A | | 2/1988 | Wirth et al. |
| 4,729,652 A | * | 3/1988 | Effert .......................... 351/210 |
| 4,996,412 A | * | 2/1991 | Anafi et al. ................ 250/201.9 |
| 5,066,116 A | * | 11/1991 | Sekine ......................... 351/221 |
| 5,258,791 A | | 11/1993 | Penney et al. |
| 5,493,391 A | | 2/1996 | Neal et al. |
| 5,526,072 A | * | 6/1996 | El Hage ....................... 351/208 |

(List continued on next page.)

FOREIGN PATENT DOCUMENTS

| | | |
|---|---|---|
| DE | 42 22 395 A1 | 1/1994 |
| EP | 0 373 788 A2 | 6/1990 |
| EP | 0 625 332 A2 | 11/1994 |
| WO | WO 83/02716 | 8/1983 |
| WO | WO 01/28408 A2 | 4/2001 |
| WO | WO 01/78585 | 10/2001 |
| WO | WO 01/82228 A2 | 11/2001 |
| WO | WO 01/89372 A2 | 11/2001 |

OTHER PUBLICATIONS

Brown, et al.; Measurement of the dynamic deformation of a high frequency scanning mirror using a Shack–Hartmann wavefront sensor; SPIE's 46th Annual Meeting International Symposium on Optical Science and Technology Jul. 29–Aug. 3, 2001; pp. 1–9.

Neal et al.; 20th AIAA 98–2701 Shack–Hartmann wavefront sensor testing of aero–optic phenomena; AIAA Advanced Measurement and Ground Testing Technology Conference Jun. 15–18, 1998, pp. 1–13.

Daniel R. Neal et al.; Application of Shack–Hartmann Wavefront Sensors to Optical System Calibration and Alignment; pp. 234–240.

(List continued on next page.)

*Primary Examiner*—Marvin M. Lateef
*Assistant Examiner*—John R. Sanders
(74) *Attorney, Agent, or Firm*—Volentine Francos, PLLC

(57) ABSTRACT

An ophthalmic error measurement system includes a projecting optical system delivering light onto a retina of an eye, a pre-correction system which compensates a light beam to be injected into the eye for aberrations in the eye, the pre-correction system being positioned in between the projecting optical system and the eye, an imaging system which collects light scattered by the retina, and a detector receiving light returned by the retina from the imaging system. Use of the pre-correction system allows the end-to-end aberrations of the ocular system to be analyzed. The use of a pre-correction system also allows use of a minimized spot size on the retina, and all of its attendant advantages.

63 Claims, 6 Drawing Sheets

U.S. PATENT DOCUMENTS

| | | | |
|---|---|---|---|
| 5,777,719 A | * 7/1998 | Williams et al. | 351/212 |
| 5,815,242 A | * 9/1998 | Anderson et al. | 351/221 |
| 5,831,712 A | * 11/1998 | Tabata et al. | 351/158 |
| 5,929,970 A | 7/1999 | Mihashi | |
| 5,936,720 A | 8/1999 | Neal et al. | |
| 5,949,521 A | * 9/1999 | Williams et al. | 351/246 |
| 5,978,053 A | 11/1999 | Giles et al. | |
| 6,052,180 A | 4/2000 | Neal et al. | |
| 6,130,419 A | 10/2000 | Neal | |
| 6,095,651 A | 11/2000 | Williams et al. | |
| 6,199,986 B1 | 3/2001 | Williams et al. | |
| 6,270,221 B1 | 8/2001 | Liang et al. | |
| 6,271,914 B1 | 8/2001 | Frey et al. | |
| 6,271,915 B1 | 8/2001 | Frey et al. | |
| 6,299,311 B1 | 10/2001 | Williams et al. | |
| 6,382,795 B1 | 5/2002 | Lai | |
| 6,394,605 B1 | 5/2002 | Campin et al. | |

OTHER PUBLICATIONS

Daniel R. Neal et al.; Characterization of Infrared Laser Systems; SPIE 3437–05 (1998); pp. 1–11.

Daniel R. Neal et al.; Amplitude and phase beam characterization using a two–dimensional wavefront sensor; SPIE vol. 2870, 0–8194–2267–3/96; pp. 72–82.

Daniel R. Neal et al.; Use of beam parameters in optical component testing; 4451, pp. 394–405.

D.R. Neal et al.; Wavefront sensors for optical diagnostics in fluid mechanics: application to heated flow, turbulence and droplet evaporation; SPIE vol. 2005, 0–8194–1254–6/93; pp. 194–203.

Lindlein et al.; Algorithm for expanding the dynamic range of a Shack–Hartmann sensor by using a spatial light modulator array; Optical Engineering, vol. 40 No. 5 May 2001; pp. 837–840.

Suzuki et al.; Error analysis of a Shack–Hartmann wavefront sensor; SPIE vol. 2443, 0–8194–1792–0/95; pp. 798–805.

Platt et al.; History and Principles of Shack–Hartmann Wavefront Sensing; Journal of Refractive Surgery, vol. 17, Sep./Oct. 2001; pp. S573–S577.

Lindlein, et al.; Experimental results for expanding the dynamic range of a Shack–Hartmann sensor using astigmatic microlenses; Optical Engineering, vol. 41 No. 2, Feb. 2002; pp. 529–533.

Lindlein et al.; Absolute sphericity measurement: a comparative study of the use of interferometry and a Shack–Hartmann sensor; Optics Letters/vol. 23, No. 10/May 15, 1998; pp. 742–744.

Lindlein et al.; Dynamic range expansion of a Shack–Hartmann sensor by use of a modified unwrapping algorithm; Optics Letters/vol. 23, No. 13/Jul. 1, 1998; pp. 995–997.

Geary, Joseph M., Introduction to Wavefront Sensors, SPIE Press, vol. TT18, copyright 1995, pp. 93–95.

International Search Report printed Nov. 26, 2001, pp. 1 and 2.

* cited by examiner

FIG. 2
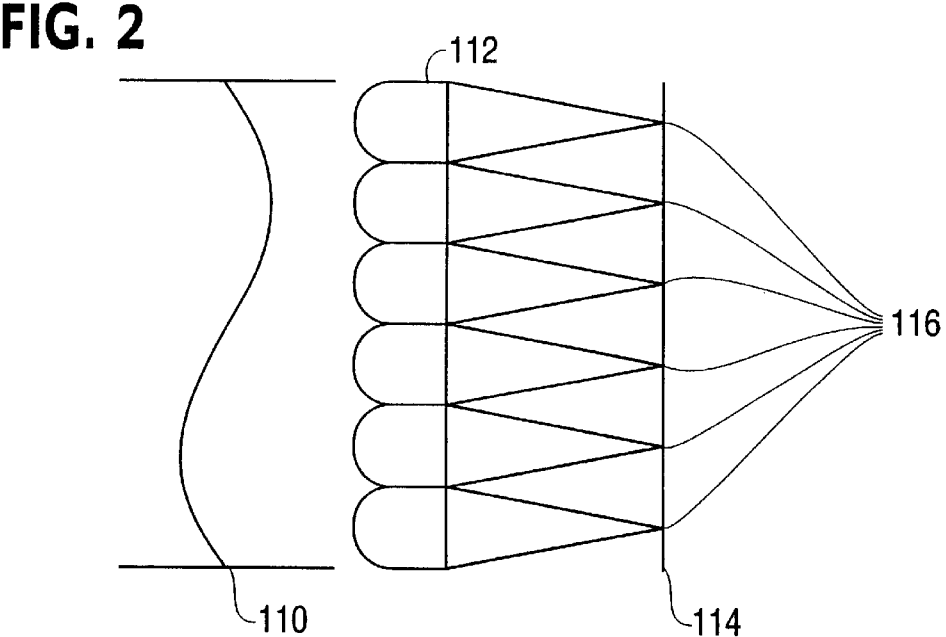
FIG. 3
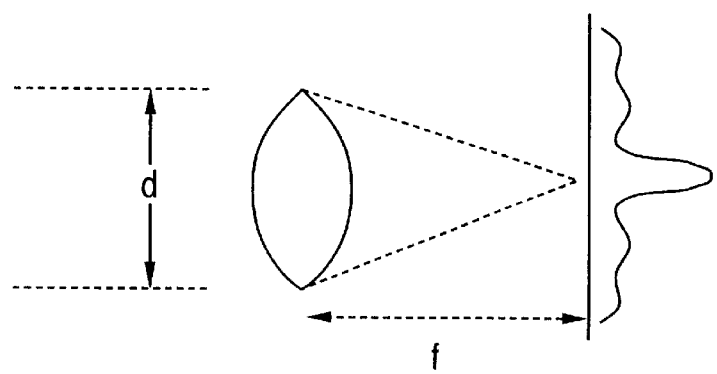
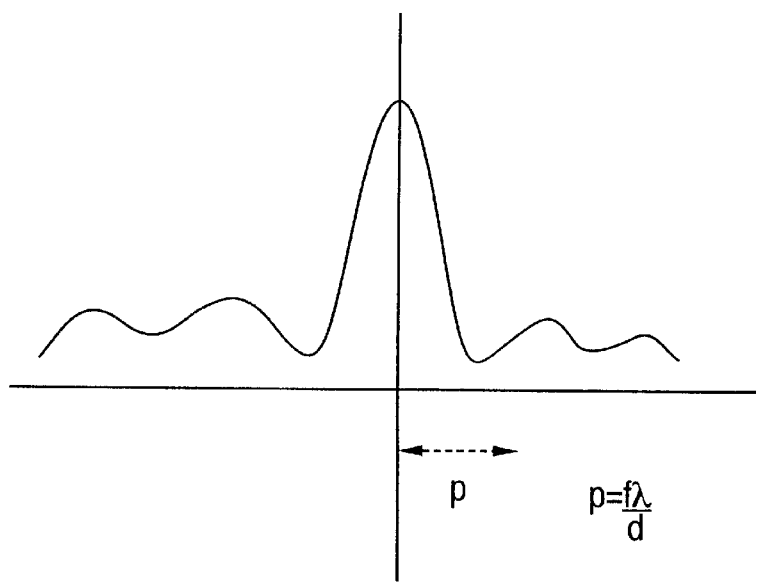
$p = \dfrac{f\lambda}{d}$

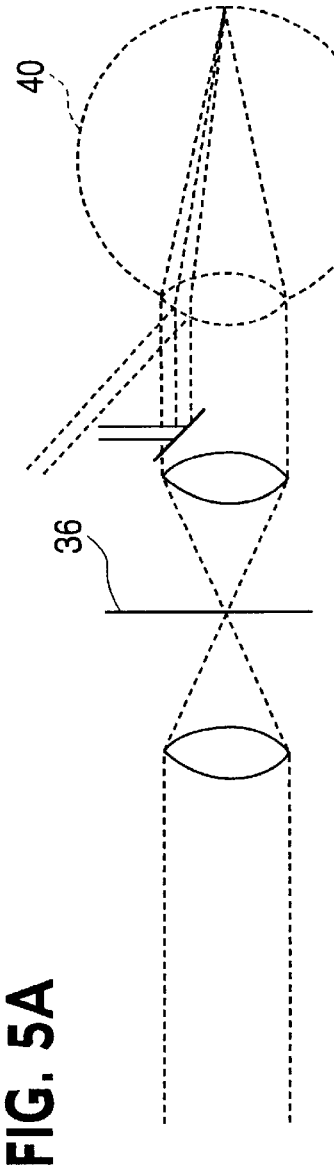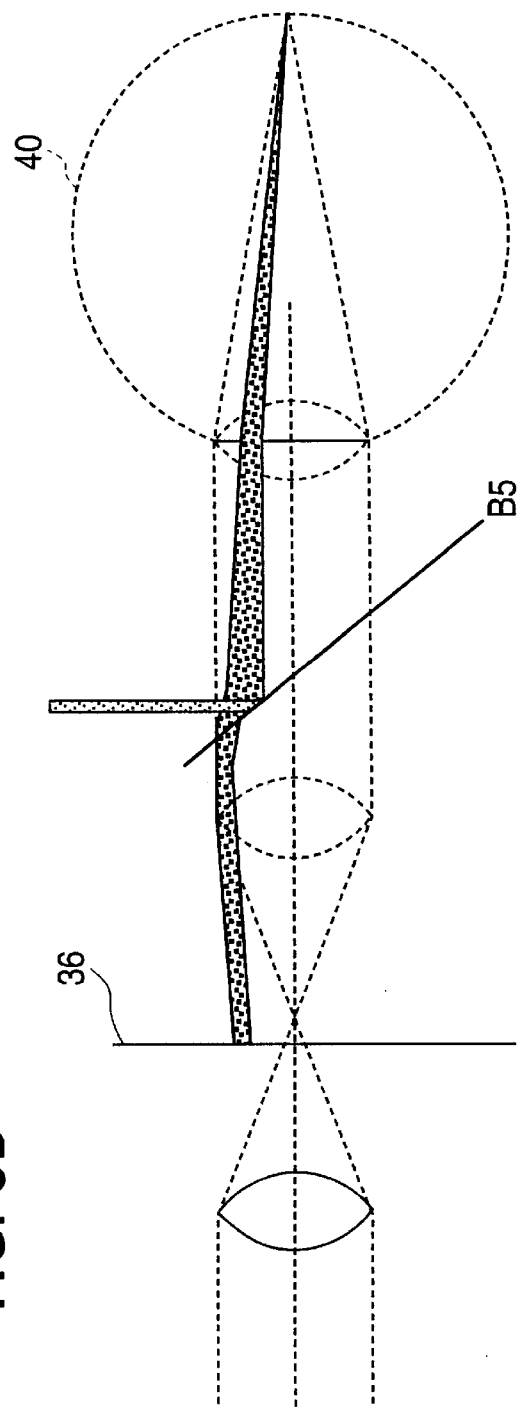
FIG. 5A
FIG. 5B

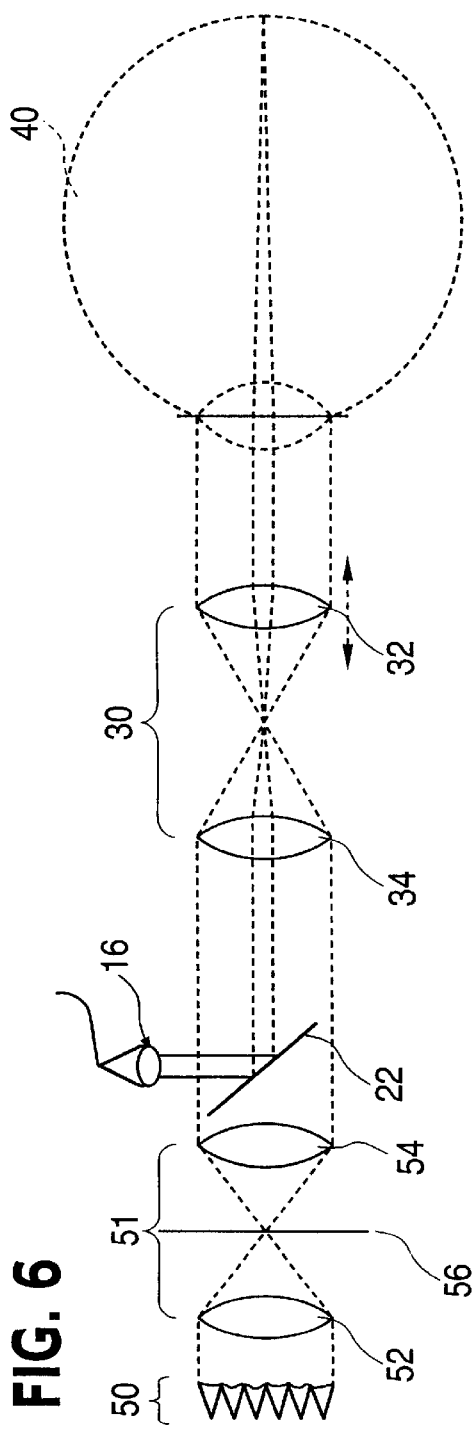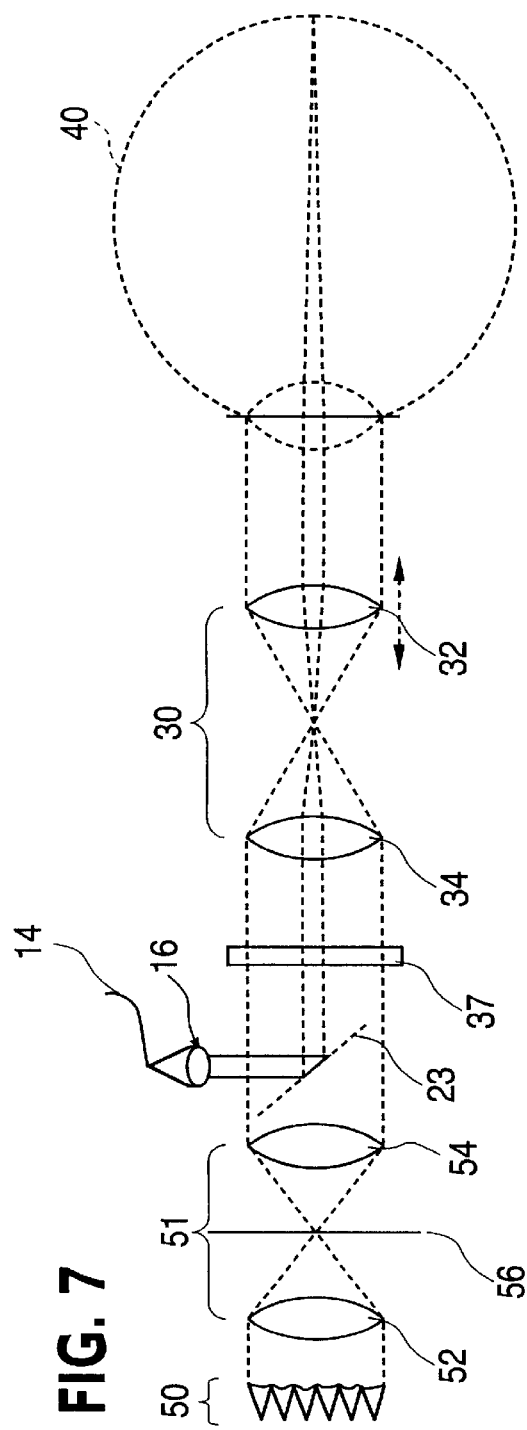

DYNAMIC RANGE EXTENSION TECHNIQUES FOR A WAVEFRONT SENSOR INCLUDING USE IN OPHTHALMIC MEASUREMENT

CROSS-REFERENCES TO RELATED APPLICATIONS

The present application claims priority under 35 U.S.C. §119 to U.S. Provisional Patent Application No. 60/182,088 filed on Feb. 11, 2000, the entire contents of which no are hereby incorporated by reference for all purposes.

BACKGROUND OF THE INVENTION

1. Field of the Invention

The present invention is directed to measurement of the refractive error in the eye, more particularly to methods and techniques for compiling a topographic mapping of these refractive errors.

2. Description of Related Art

Measurements of aberrations in an eye are important for diagnosis of visual defects and assessment of acuity. These measurements and their accuracy become increasingly important in light of the growing number of ways, both surgical and non-surgical, that aberrations can be corrected. These corrections rely on accurate, precise measurements of the entire ocular system, allowing successful screening, treatment and follow-up. Enhancements in the accuracy of ocular measurements may aid in improving the identification of patients in need of correction and the performance of the correction itself.

There are a number of current methods used to measure performance of the ocular system. The most widely used and well established are psycho-physical methods, i.e., methods relying on subjective patient feedback. The oldest of the psycho-physical methods is the foreopter or trial lens method, which relies on trial and error to determine the required correction. There are psycho-physical methods for measuring visual acuity, ocular modulation transfer function, contrast sensitivity and other parameters of interest.

In addition to these subjective methods, there are also objective methods for assessing the performance of the ocular system. Such objective methods include corneal topography, wavefront aberrometry, corneal interferometry, and auto-refraction. Many of these methods only measure the contribution of specific elements to the total refractive error. For example, much work has been directed to measuring the topography of the cornea and characterizing the corneal layer. However, the corneal shape only contributes about 30–40% of the total refractive error in most cases. In order to measure the bulk of the refractive error and to provide a complete mapping for diagnosis and correction, additional information and measurements are needed.

Another method for determining the refraction of the eye is auto-refraction, which uses a variety of techniques to automatically determine the required corrective prescription. These automated techniques include projecting one or more spots or patterns onto the retina, automatically adjusting optical elements in the auto-refractor until the desired response is achieved, and determining the required correction from this adjustment. However, auto-refractors are not considered especially reliable. Further, auto-refractors measure only lower order components of the aberrations, e.g., focus and astigmatic errors.

Recently, the eye has started being considered as an optical system, leading to the application of methods previously used for other optical systems to the measurement of the eye. These methods include interferometry and Shack-Hartmann wavefront sensing. These techniques are of particular interest because they measure the complete aberrations of the eye. This additional information allows measurement of non-uniform, asymmetric errors that may be affecting vision. Further, this information may be linked with any of the various corrective techniques to provide improved vision. For example, U.S. Pat. No. 5,777,719 to Williams describes the application of Shack-Hartmann wavefront sensing and adaptive optics for correcting ocular aberrations to make a super-resolution retina-scope. U.S. Pat. No. 5,949,521 to Williams et al. describes using this information to make better contacts, intra-ocular lenses and other optical elements.

Wavefront aberrometry measures the full, end-to-end aberrations through the entire optics of the eye. In these measurements, a spot is projected onto the retina, and the resulting returned light is measured with an optical system, thus obtaining a full, integrated, line-of-sight measurement of the eye's aberrations. A key limitation of the instruments used in these measurements is the total resolution, which is ultimately limited by the lenslet array of the instrument. However, selection of the lenslet array is itself limited by several factors, most importantly the size of the spot projected onto the retina.

A schematic illustration of the basic elements of a two dimensional embodiment of a Shack-Hartmann wavefront sensor is shown in FIG. 2. A portion of an incoming wavefront 110 from the retina is incident on a two-dimensional lenslet array 112. The lenslet array 112 dissects the incoming wavefront 110 into a number of small samples. The smaller the lenslet, the higher the spatial resolution of the sensor. However, the spot size from a small lenslet, due to diffraction effects, limits the focal length that may be used, which in turn leads to lower sensitivity. Thus, these two parameters must be balanced in accordance with desired measurement performance.

Mathematically, the image on the detector plane 114 consists of a pattern of focal spots 116 with regular spacing d created with lenslets 112 of focal length f, as shown in FIG. 3. These spots must be distinct and separate, i.e., they must be readily identifiable. Thus, the spot size $\rho$ cannot exceed ½ of the separation of the spots. The spot separation parameter $N_{FR}$ can be used to characterize the lenslet array 12 and is given by:

$$N_{FR} = \frac{d}{\rho} \qquad (1)$$

The relationship between the size of a lens and the focal spot it creates, where $\lambda$ is the wavelength of the light, is given by:

$$\rho = 1.22 f \frac{\lambda}{d} \qquad (2)$$

for a round lens or $$\rho = \frac{f\lambda}{d} \qquad (3)$$

for a square lens. Thus, for a square lens, the separation parameter can be given by:

$$N_{FR} = \frac{d^2}{f\lambda} \quad (4)$$

This is also known as the Fresnel number of the lenslet. To avoid overlapping focal spots, $N_{FR}>2$. In practice, the Fresnel number must be somewhat greater than two to allow for a certain dynamic range of the instrument. The dynamic range of a Shack-Hartmann wavefront sensor can be defined as the limiting travel of the focal spot such that the edge of the spot just touches the projected lenslet boundary, given by:

$$\theta_{max} = \frac{\frac{d}{2} - \rho}{f} \text{ or} \quad (5)$$

$$\theta_{max} = \frac{d}{2f} - \frac{\lambda}{d} = \left[\frac{N_{FR}}{2} - 1\right]\frac{\lambda}{d} \quad (6)$$

Thus, the dynamic range is directly proportional to the separation parameter and the lenslet size.

A particularly useful arrangement for a Shack-Hartmann wavefront sensor ocular measuring system places the lenslet array in an image relay optical system at a plane conjugate to the pupil or corneal surface. In this configuration, the spot size on the detector of the wavefront sensor is given by:

$$\rho_2 = \frac{1}{M}\frac{f_L}{f_e}\rho_1 \quad (7)$$

where M is the magnification of the imaging optics, $f_L$ is the focal length of the lenslet array, $f_e$ is the focal length of the eye and $\rho_1$ is the spot size on the retina.

Comparing Equations (5) and (7), it is evident that the dynamic range of the wavefront sensor is limited by the size of the spot $\rho_1$ projected on the retina. For a practical system, the dynamic range must be able to resolve errors in the optical systems. Thus, the dynamic range is a key limited parameter of the entire system design. In previous implementations of the Shack-Hartmann wavefront sensor used for ocular measurement, the dynamic range has been increased by increasing the size of each lenslet. However, the eye itself can have significant aberrations. Thus, any beam projected into the eye will become aberrated, spreading the focal spot and increasing the spot size $\rho_1$ on the retina.

Various techniques have been implemented to address this problem. A small diameter beam has been used so that the total wavefront error is minimized across the injected beam. Another proposed solution projects the light into the eye at the focal point of a long focal length lens, operating as a field lens so that the size of the focal spot is not affected by the eye aberrations. In practice, for both of these cases, the beam is still somewhat large and is increased in size by the aberrations of the ocular system.

Another limitation on the dynamic range of the system is the sampling size. With a large spot on the retina, the sample size of the wavefront sensor must be increased to allow even a minimal dynamic range to be realized. For ocular systems with strong aberrations, such as found in people with large astigmatism or for those having undergone LASIK, the aberrations over each lenslet are sufficient to degrade the lenslet focal spot. Thus, the system is limited not just by focal spot overlap, but by the fact that the focal spots themselves fade out or are difficult to track. Using a small sample size does not allow sufficient light to be gathered, since the light is scattered by the retina into a large number of focal spots. Due to safety considerations, the input power may not be increased to compensate for this scattering.

SUMMARY OF THE INVENTION

The present invention is therefore directed to measurement of refractive errors of an eye that substantially overcomes one or more of the problems due to the limitations and disadvantages of measurements of the related art.

It is an object of the present invention to measure the end-to-end aberrations of the eye with sufficient accuracy and dynamic range in a practical manner.

It is a further object of the present invention to project a light beam into an ocular system so as to minimize the size of the focal spot on the retina.

It is another object of the present invention to use this smaller focal spot to allow much greater sampling density of the ocular system, thereby enhancing the accuracy and dynamic range.

It is yet another object of the present invention to make a practical, low cost system, available for use in a clinical setting.

At least one of the above and other objects may be realized by providing a system for measuring errors in an eye including a projecting optical system which delivers light onto a retina of the eye, a pre-correction system which compensates a light beam to be injected into the eye for aberrations in the eye, the pre-correction system being positioned in between the projecting optical system and the eye, an imaging system which collects light scattered by the retina, and a detector receiving light from the retina collected by the imaging system.

The detector may be a Shack-Hartmann wavefront sensor, a shearing interferometer, a Moire deflectometer, or other passive phase measurement systems. The pre-correction system may include a telescope having at least one movable lens, fixed lenses inserted at an intermediate image plane, adaptive optical elements, and/or a cylindrical telescope. The pre-correction system may correct for focus and/or astigmatism errors in the eye. The telescope may be arranged so that a fixed lens of the telescope is one focal length away from the eye. Components used in the pre-correction system may also be used in the imaging system.

The pre-correction system may include a feedback loop which determines an appropriate pre-correction to be supplied by the pre-correction system. The feedback loop may include a detector receiving light returned from the retina, a processor comparing detected light with a desired feature of the light and adjusting at least one parameter of the pre-correction system in accordance with the comparison. The feedback loop may further include a return optical system for gathering the light from the retina. The return optical system may include the pre-correction system. The desired feature may be a minimized spot size on the retina.

The system may include an aperture that limits the angular dynamic range of the system. The system may further include a polarizing beam splitter between the eye and the wavefront sensor. The system may include an aligner that determines an appropriate eye alignment of the system. The projecting optical system may provide light to the eye at an angle to a central axis of the eye. The system may include an additional optical system between the detector and the eye. The system may include a power monitor which monitors power of the light beam being injected in the eye. The system may include an eye position detection system including a target projected on the eye, a position detector sensing the eye, and an adjustment system which adjusts a position of the system relative to the eye until the eye is in focus on the detector.

These and other objects of the present invention will become more readily apparent from the detailed description given hereinafter. However, it should be understood that the detailed description and specific examples, while indicating the preferred embodiments of the invention, are given by way of illustration only, since various changes and modifications within the spirit and scope of the invention will become apparent to those skilled in the art from this detailed description.

BRIEF DESCRIPTION OF THE DRAWINGS

The foregoing and other objects, aspects and advantages will be described with reference to the drawings, in which:

FIG. 2 is a schematic side view of the basic components of a Shack-Hartmann wavefront sensor;

FIG. 3 schematically illustrates the relationship between the size of the lens, its focal length and the spot size;

FIGS. 5A–5B schematically illustrate off-axis injection of the light into the eye and the blocking of the reflected light from entering the wavefront sensor;

FIG. 6 is a schematic illustration of a configuration of the present invention using a fixed telescope and an adjustable telescope;

FIG. 7 is a schematic illustration of a configuration of the present invention using a variable lens;

DETAILED DESCRIPTION OF THE PREFERRED EMBODIMENTS

As noted above, the key to designing a practical ocular wavefront sensor system is how the light is injected into the eye. Since ocular refractive errors can be large, e.g., up to 20 diopters, the degradation of the injected beam can be significant. Further, it is difficult to design a wavefront sensor that has sufficient range to directly measure an extremely large refractive error. In accordance with the present invention, the spot projected on the ocular system is pre-distorted in a manner that compensates for the eye's fundamental aberrations. This allows the spot returned to the wavefront sensor to be well formed and minimally affected by the refractive errors. The small size of the spot allows small lenslets to be used while maintaining sufficient dynamic range to measure even large, high order aberrations. Since the light is tightly focused on the retina, the light is only scattered from a small region. When this small region is imaged onto the focal plane of the wavefront sensor, the light is concentrated onto a small group of pixels. Thus, even though the reflected light must be divided among a larger number of lenslets, each focal spot is brighter than in the conventional methods. Further, the greater sampling density leads to smaller wavefront aberrations across the aperture of each lenslet.

Figure 1:
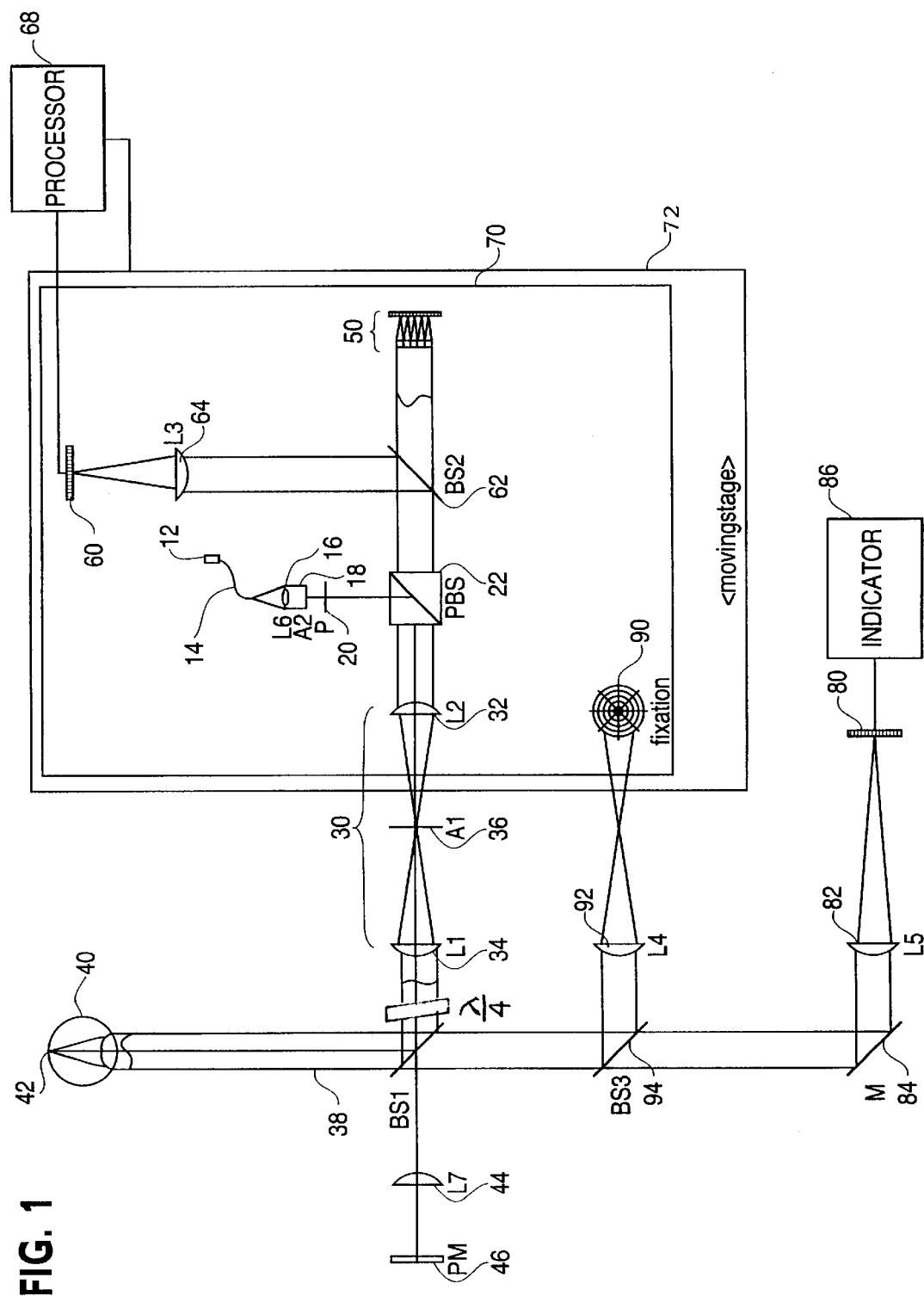
FIG. 1 is a schematic top view of the measurement system of the present invention.

A system for such error measurement employing pre-compensation is shown in FIG. 1. The ocular wavefront measurement system shown therein generally includes a projection system for projecting light into the eye, a system for pre-correcting the injected light for ocular aberrations, a system for collecting light, a system for determining the pre-correction, and a system for measuring the collected light.

The projection system shown in FIG. 1 includes a light source 12, e.g., a laser, a laser diode, LED, or a superluminescent diode, supplied to an optical fiber 14. For safety reasons, the light source is preferably a pulsed light source, is limited to a small power, is outside the normal visual detection range, e.g. infrared, and/or is directly collimated with an appropriate lens. The optical fiber may be a polarization maintaining fiber. The light leaving the optical fiber 14 is provided to a collimating lens 16. The use of an optical fiber 14 to deliver light from the light source 12 simplifies the collimating lens 16, since the fiber exit mode acts as a diffraction-limited point source. The collimating lens 16 is preferably rigidly mounted to the fiber 14. The collimated beam is then truncated to a desired size by an aperture 18. If needed, a polarizer 20 may be provided for polarizing the collimated beam. A polarizing beam splitter 22 directs the light from the projection system to the rest of the ocular measuring system.

Alternatively, the light source 12 may be provided alone, i.e., without the use of the fiber 14. The light from the light source 12 itself is then collimated by a collimating lens. While light sources used for ophthalmic measurement typically have a high degree of astigmatism, by using only a portion of the beam, e.g., 10–25%, typically from the center of the beam, the wavefront error over the beam is small enough that the beam size is substantially stable over the distance traversed in the ophthalmic measurement system. In other words, even though the beam is still astigmatic, the beam shape does not change while traversing the ophthalmic measurement system due to this astigmatism, so the astigmatism does not influence the measurement. The light may be polarized as required.

The light from the projection system is reflected by the polarizing beam splitter 22 and directed to a pre-compensation system, shown in FIG. 1 as a telescope 30. The telescope includes lenses 32, 34 with an aperture 36 in between. The telescope 30 may be adjusted by moving the lenses relative to one another. This adjustment is to provide the desired pre-correction for the injected beam by adding defocus that just compensates for the spherical equivalent defocus of the ocular system being measured. The light from the telescope is directed by a beam splitter 38 to an ocular system 40 under measurement. The injected beam is focused by the ocular system 40 to a focal spot 42 on the retina of the ocular system 40. Light from this focal spot 42 is scattered or reflected by the retina.

The returned light is collected by the cornea and lens of the ocular system 40 and is approximately collimated. The beam splitter 38 directs the beam from the ocular system back to the telescope 30. The same position of the lenses 32, 34 of the telescope 30 corrects for the defocus aberrations of the ocular system 40 so that light arrives at a wavefront sensor 50 collimated to within the dynamic range of the sensor. The aperture 36 blocks any rays outside the angular dynamic range of the wavefront sensor 50 so that no mixing or measurement confusion occurs. When the wavefront sensor 50 is a Shack-Hartmann sensor, the focal spots cannot collide, interfere or cause confusion with adjacent focal spots. The light from the telescope now passes through the polarizing beam splitter 22, since the interaction with the retina will rotate the polarization of the light from the input polarization. The wavefront sensor 50 may be a Shack-Hartmann wavefront sensor, a shearing interferometer, a Moire deflectometer or any other passive phase measurement sensor. When the wavefront sensor 50 is a Shack-Hartmann wavefront sensor, the wavefront sensor 50 includes the elements shown in FIG. 2.

The proper position of the lenses 32, 34 of the telescope 30 may be determined in a number of ways. In a preferred embodiment, an additional sensor 60 is used with a beam splitter 62 and a focusing lens 64 to create an image of the light incident upon the retina. The proper position of the lenses 32, 34 in the telescope 30 is determined by minimizing the spot size 42 on the back of the retina, performed by comparing the spot sizes from different positions of the lenses 32, 34 in the telescope 30. If the ocular system 40 is arranged to be one focal length of the objective lens 34 away from the lens 34, then the telescope 30 will be insensitive to changes in magnification or other errors. The wavefront sensor 50 should be arranged to be at the conjugate image plane to the ocular system 40. Preferably, the wavefront sensor 50, the retinal imaging sensor 60, the projection optics 16, 18, 20, the polarizing beam splitter 22, the beam splitter 62, and the focusing lens 64 are mounted on a platform 70 which is mounted in a moving stage 72. This allows the relative position of the telescope lenses 32, 34 to be varied while fixing the position of the remaining elements on the platform 70. The use of the optical fiber 14 allows the light source to be mounted off the platform 70, minimizing the mass of the elements moved by the translation stage 72. A processor 68 may be included to control movement of the translation stage 72 and to allow data processing, analysis and/or display.

As an additional safety measure, a small portion of the beam incident on beam splitter 38 is transmitted to a lens 44 which focuses the light onto a power monitor 46. The output of this power monitor 46 may be used to shut down the system if the power exceeds the safety limits of the system or to alter the power supplied to the light source 12 to reduce the power output by the light source in a known manner.

To measure the proper eye position relative to the measuring system, an additional detector 80 is included. Imaging optics 82 are designed such that the iris or cornea will be in focus for only a narrow region of space. A mirror 84 may be used to direct light onto the iris detector 80. The position of the system relative to the eye is adjusted until the iris or cornea is detected. The detection may be indicated to a user on an indicator 86. Preferably, this detection is used just during patient alignment and only uses a small percentage, e.g., less than 10% of the light.

To insure that the patient is viewing the correct line of sight, a target 90 is made visible through a beam splitter 94. The target 90 is imaged at infinity through a lens 92. The target position may be varied by moving the target relative to the lens 92 to present targets that are either in focus or slightly out-of-focus to minimize patient accommodation. Movement of the target 90 closer to the lens 92 stimulates near vision accommodation, allowing measurement of near vision visual acuity or the target may be arranged with the image past infinity to measure distance vision. The patient merely attempts to focus on the target. A light source behind the target is electronically controlled to adjust the target brightness and the position of the target is also electronically adjustable.

Thus, the telescope 30 is used to pre-compensate the injected light and to compensate for the returned wavefront to minimize the total wavefront error incident on the wavefront sensor. In the related art, telescopes have been used to perform relay imaging of the light onto the wavefront sensor and to compensate for strong spherical and cylindrical aberrations, but the light was injected separately. This separate handling is due to strong back reflections that occur even for lenses having anti-reflection coatings thereon. Since the returned light from the retina may be very weak, even a small reflection from the lenses can quickly dominate the measurement and saturate the wavefront sensor 50. There are several ways of dealing with the problem. First, as shown in FIG. 1, polarized light and a polarizing beam splitter in conjunction with a quarter-wave plate may be used. Off axis parabolas or other curved mirrors may be used to direct the light to the telescope. The light may be injected off axis, so that any reflected light from the cornea is filtered out by the apertures of the system, as shown in FIGS. 5A and 5B. FIG. 5B illustrates how the light reflected by the cornea of the eye 40 is blocked by the aperture 36 from entering the wavefront sensor and influencing the measurement. The use of one or more of these schemes is sufficient to allow pre-compensation of the injected beam in accordance with the present invention without introducing unwanted reflections.

As an alternative, a second telescope may be used in conjunction with the first telescope to increase the dynamic range by providing an alternative location for the filtering aperture. Thus, one telescope can be completely fixed, while the other has a degree of freedom allowing movement until the lenses of the two telescopes are in contact. Such a configuration is shown in FIG. 6, in which a fixed telescope 51 with lenses 52, 54 and aperture 56, is used to supply light to the wavefront sensor 50. This is in conjunction with the elements discussed above regarding FIG. 1. For simplicity, only the essential elements of the light delivery system 14, the collimating lens 16, the polarizing beam splitter 22, the adjustable telescope 30, and the eye 40, have been shown.

Figure 8:
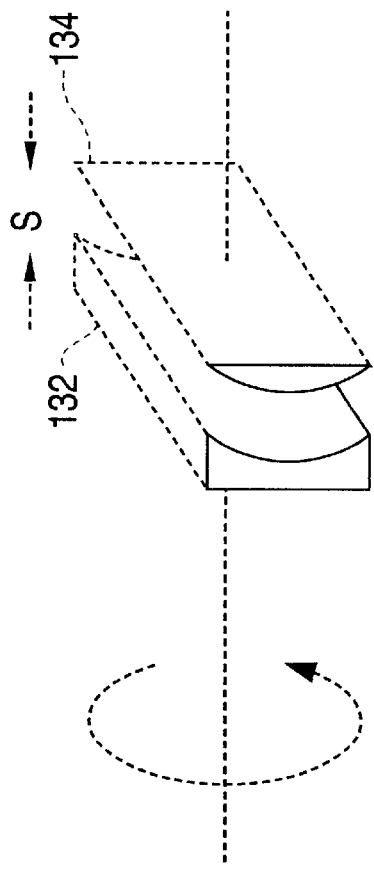
FIG. 8 is a schematic illustration of a cylindrical telescope for use with the present invention.

Compensation of astigmatism of the ocular system and of the injected beam may be achieved in the following ways. The telescope 30 may be a cylindrical lens telescope or a pair of positive and negative lenses. Such a cylindrical lens configuration is shown in FIG. 8, in which a pair of cylindrical lenses 132, 134 is used in place of lenses 32, 34. The spacing s between the lenses may be adjusted to increase or decrease power of the telescope. The angle of the pair 120, 122 is adjusted relative to the axis of the transmission path. This complicates the instrument, but provides for a better beam projected into the eye, requiring a wavefront sensor of only limited dynamic range, since both spherical and cylindrical aberrations would be subtracted from the wavefront, and only higher order terms would remain.

Alternatively, a high dynamic range wavefront sensor can be used. Since, in accordance with the present invention, only a small beam is injected into the eye, which will only pick up only a small wavefront aberration across its aperture, the focal spot on the eye will still be quite small, even with some astigmatism. Thus, cylindrical compensation is usually not needed. While some distortion will take place, it will be limited in size and an adequately small spot will still be realized. A high dynamic range wavefront sensor corresponds to the use of a smaller focal length for the wavefront sensor lenslet array, as set forth in Equations (3) and (7). While the use of only spherical lenses will result in a loss of accuracy, the larger number of measurements afforded by the smaller lenslet array will sufficiently compensate for this degradation.

Figure 9:
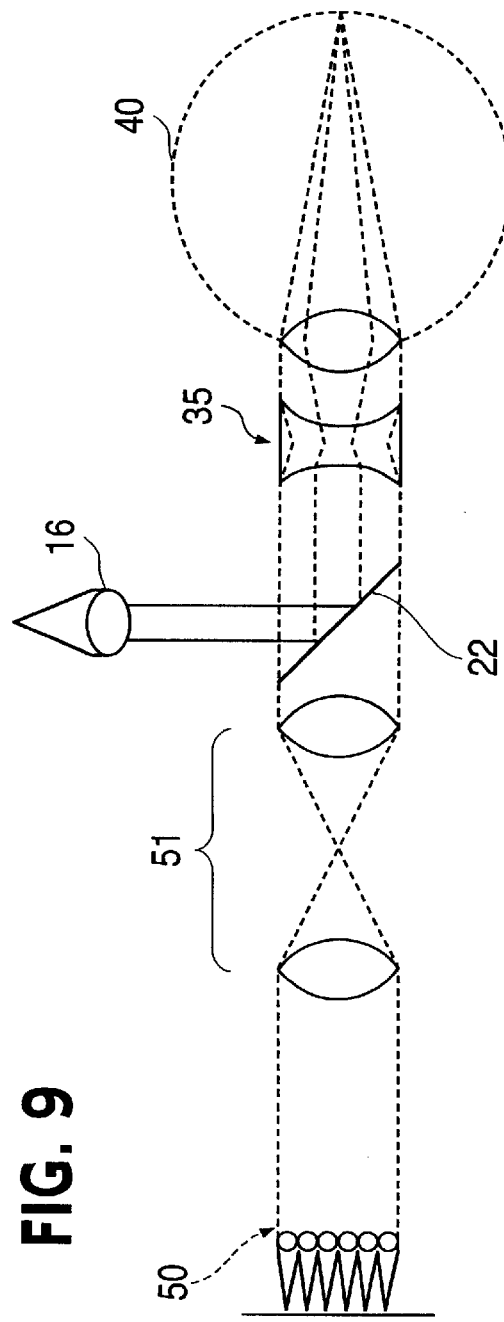
FIG. 9 is a schematic illustration of a configuration of the present invention using a corrective lens.

An alternative to using the telescope with a movable lens, as shown in FIG. 1, for correcting base aberrations of the eye in the injected and reflected wavefront includes placing a corrective lens in front of the eye. If this lens is not a contact lens, it cannot be placed at the actual pupil plane of the eye, as shown in FIG. 9, in which a corrective lens 35 is placed adjacent to the eye 40. Thus, there will always be some magnification introduced by the combination of the refractive error of the eye and the correcting lens. Since it is difficult to set or know the vertex distance of the corrective lens, this magnification would be poorly known at best, and introduce error into the entire measurement.

Figure 4A:
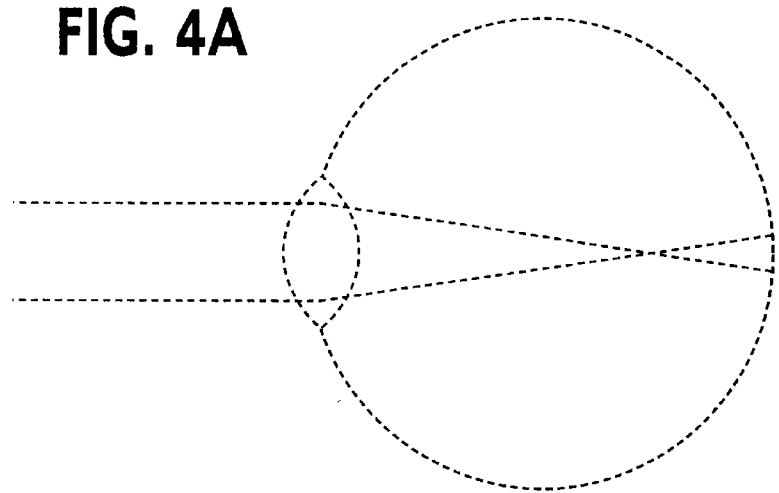
FIGS. 4A–4C schematically illustrate the spot size for different configurations.
Figure 4B:
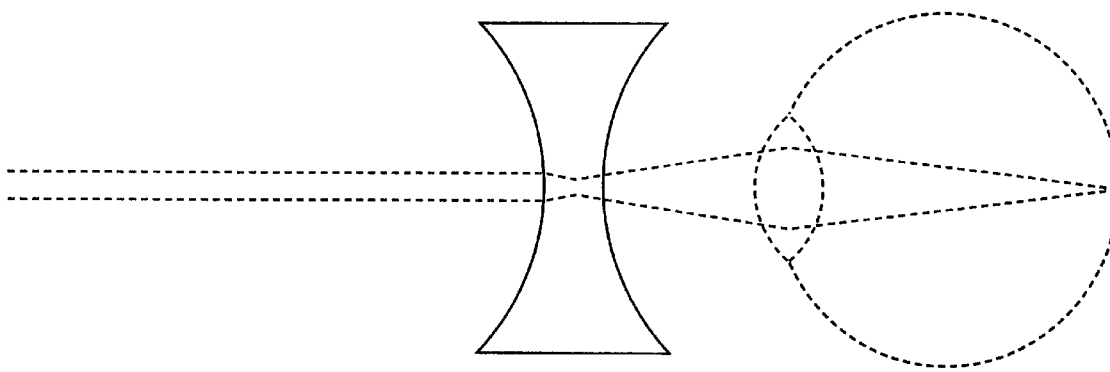
Figure 4C:
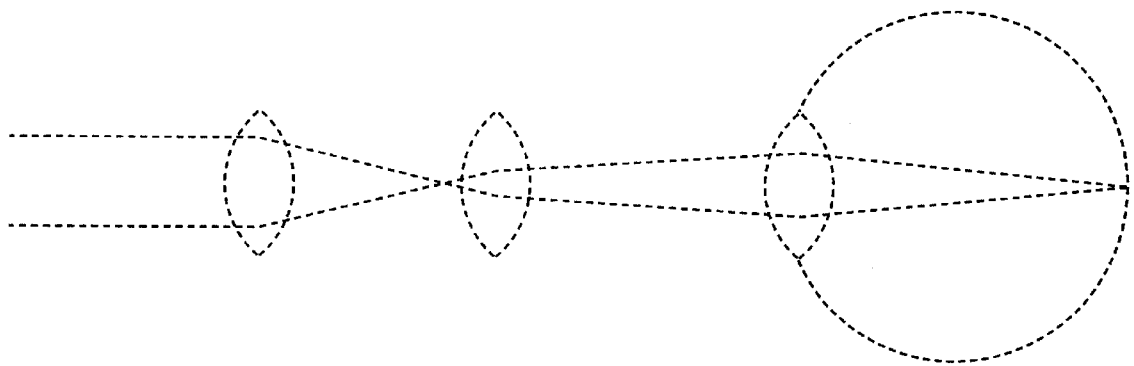

Another alternative includes using fixed or variable lenses. Ideally, these lenses are placed at an optical plane that is conjugate to the surface of the eye. Since it is also desirable for the wavefront sensor to be at this plane, a second telescope will need to be used in series with the first telescope. Further, since all of the lenses are fixed, some means will be needed for changing the various pre-corrector lenses in a known manner to achieve the proper result. A lens 37 in FIG. 7 may be from a trial lens kit, such as is commonly used for measuring a patient's manifest refraction, but is limited to the prescription accuracy. Alternatively, the lens 37 in FIG. 7 may be a variable focal length lens, e.g., adaptive optics, liquid crystal displays, deformable mirrors. The focal lengths of these elements may be controlled electronically, e.g., by the processor 68 shown in FIG. 1, rather than by movement. Either of these configurations is shown in FIG. 7, in which the lens 37 may be a trial lens or a variable focal length lens. The applicability of these configurations and the telescope configuration is shown in FIGS. 4A–4C, in which the size of the spot in a myopic eye alone is shown in FIG. 4A, the size of the spot size with correction with a lens 37 is shown in FIG. 4B and the spot size with the adjustable telescope 30 is shown in FIG. 4C. As can be seen, both configurations in FIGS. 4B and 4C result in the desired small spot size of the present invention.

By pre-compensating for aberrations of the eye in the injected beam in accordance with the present invention, a small focal spot can be created on the retina. This small focal spot will concentrate light more, allowing the light to be divided into a larger number of focal spots. This, in turn, allows higher spatial resolution and the use of lower injected light power. Higher spatial resolution means that the assumption that each lenslet measures only tilt is valid over a much larger range. Higher spatial resolution also leads to greater dynamic range and accuracy. Higher dynamic range, means that measurement of even high order terms of aberration can be accomplished accurately, without significant degradation of the measurement.

While the present invention is described herein with reference to illustrative embodiments for particular applications, it should be understood that the present invention is not limited thereto. Those having ordinary skill in the art and access to the teachings provided herein will recognize additional modifications, applications, and embodiments within the scope thereof and additional fields in which the invention would be of significant utility without undue experimentation. Thus, the scope of the invention should be determined by the appended claims and their legal equivalents, rather than by the examples given.

What is claimed:

1. A system for measuring errors in an eye comprising:
   a projecting optical system which delivers light onto a retina of the eye;
   a pre-correction system which compensates a light beam to be injected into the eye for aberrations in the eye, the pre-correction system being positioned in between the projecting optical system and the eye;
   an imaging system which collects light scattered by the retina; and
   a wavefront sensor receiving light returned by the retina from the imaging system.

2. The system of claim 1, wherein the wavefront sensor is a Shack-Hartmann wavefront sensor.

3. The system of claim 1, wherein the wavefront sensor is a shearing interferometer.

4. The system of claim 1, wherein the wavefront sensor is a Moire deflectometer.

5. The system of claim 1, wherein the pre-correction system comprises a telescope having at least one movable lens.

6. The system of claim 5, wherein said telescope is arranged so that a fixed lens of the telescope is one focal length away from the eye.

7. The system of claim 1, wherein the pre-correction system comprises fixed lenses inserted at an intermediate image plane.

8. The system of claim 1, wherein the pre-correction system comprises adaptive optical elements.

9. The system of claim 1, wherein the pre-correction system corrects for focus errors in the eye.

10. The system of claim 1, wherein the pre-correction system corrects for focus and astigmatism.

11. The system of claim 1, further comprising a polarizing beam splitter between the eye and the wavefront sensor.

12. The system of claim 1, further comprising an aligner that determines an appropriate eye alignment of the system.

13. The system of claim 1, wherein the projecting optical system provides light to the eye at an angle to a central axis of the eye.

14. The system of claim 1, further comprising an additional optical system between the wavefront sensor and the eye.

15. The system of claim 1, further comprising a power monitor which monitors power of the light beam being injected in the eye.

16. The system of claim 1, further comprising an eye position detection system including a target projected on the eye, a position detector sensing the eye, and an adjustment system which adjusts a position of the system relative to the eye until the eye is in focus on the detector.

17. The system of claim 1, wherein the pre-correction system is a cylindrical telescope.

18. The system of claim 1, wherein components used in the pre-correction system also are used in the imaging system.

19. The system of claim 1, wherein the pre-correction system includes a feedback loop which determines an appropriate pre-correction to be supplied by the pre-correction system.

20. The system of claim 19, wherein said feedback loop includes a detector receiving light returned from the retina, a processor comparing detected light with a desired feature of the light and adjusting at least one parameter of the pre-correction system in accordance with the comparison.

21. The system of claim 20, wherein said feedback loop further includes a return optical system for gathering the light from the retina.

22. The system of claim 21, wherein the wavefront sensor is used to find an optimum telescope position.

23. The system of claim 21, wherein the wavefront sensor is used with a range limiting aperture to insure that the wavefront sensor only sees data within a dynamic range of the system.

24. The system of claim 21, wherein filtering algorithms are used to optimize convergence of a position of the telescope.

25. The system of claim 20, wherein said desired feature is a minimized spot on the retina.

26. The system of claim 1, further comprising a movable eye fixation target the retina.

27. The system for measuring errors of claim 1, wherein the pre-correction system comprises a telescope having at least one movable lens, the system for measuring errors further comprising:
  a fixation target; and
  a movable stage on which the detector, the fixation target, and the movable lens are all mounted.

28. The system for measuring errors of claim 1, wherein the wavefront sensor comprises a lenslet array and a detector, the system for measuring errors further comprising an adjustment camera adapted to aid in bringing into focus onto the detector aerial images from the lenslet array.

29. The system for measuring errors of claim 1, wherein the pre-correction system includes at least one variable focal length lens.

30. The system for measuring errors of claim 1, wherein the pre-correction system includes a processor controlling the variable focal length lens.

31. A system for measuring errors in an eye comprising:
  a projecting optical system which delivers light onto a retina of the eye;
  a pre-correction system which compensates a light beam to be injected into the eye for aberrations in the eye, the pre-correction system being positioned in between the projecting optical system and the eye;
  an imaging system which collects light scattered by the retina;
  a Shack-Hartmann wavefront sensor receiving light returned by the retina from the imaging system; and
  an aperture that limits the angular dynamic range of the system.

32. The system of claim 10, wherein the pre-correction system comprises a telescope having at least one movable lens.

33. The system of claim 31, further comprising an eye position detection system including a target projected on the eye, a position detector sensing the eye, and an adjustment system which adjusts a position of the system relative to the eye until the eye is in focus on the detector.

34. The system of claim 31, wherein the projecting optical system provides light to the eye at an angle to a central axis of the eye.

35. The system of claim 31, wherein the pre-correction system comprises a telescope having at least one movable lens, the system for measuring errors further comprising:
  a fixation target; and
  a movable stage on which the Shack-Hartmann wavefront sensor, the fixation target, and the movable lens are all mounted.

36. A wavefront sensor for determining wave aberrations of the eye, comprising:
  a lenslet array adapted to receive an image of a light spot on a retina of an eye and for creating aerial images of the light spot;
  a sensor adapted to receive the aerial images from the lenslet array;
  a processor adapted to receive signals from the sensor corresponding to the aerial images and to determine the wave aberrations from the signals; and
  an adjustment camera adapted to aid in bringing into focus onto the sensor the aerial images from the lenslet array.

37. The wavefront sensor of claim 26, further comprising a focus-adjusting lens system adapted to aid in focusing the aerial images.

38. The wavefront sensor of claim 26, further comprising a waveplate in an optical path of the wavefront sensor.

39. The wavefront sensor of claim 38, wherein the waveplate is a $\lambda/4$ waveplate.

40. The wavefront sensor of claim 36, further comprising a polarizing beamsplitter in an optical path of the wavefront sensor.

41. The wavefront sensor of claim 36, further comprising a beamsplitter adapted to reflect a whole image portion of the image of the light spot received by the adjustment camera.

42. The wavefront sensor of claim 36, wherein the lenslet array is associated with a lenslet camera and the adjustment camera is separate from the lenslet camera.

43. The wavefront sensor of claim 36, further comprising a light source adapted to provide light to the retina for forming the aerial images.

44. The wavefront sensor of claim 43, wherein the light source comprises a laser.

45. The wavefront sensor of claim 43, wherein the light source comprises a pulsed laser.

46. The wavefront sensor of claim 36, wherein the wavefront sensor is adapted to measure wavefront aberrations of the eye.

47. The wavefront sensor of claim 36, wherein the adjustment camera is adapted to aid in sharpening the aerial images.

48. The wavefront sensor of claim 36, further comprising an eye fixation target adapted to allow the patient to fixate and focus while the adjustment camera is aiding in bringing into focus the aerial images.

49. The wavefront sensor of claim 36, wherein the image of the light spot comprises an image of light backscattered from the retina.

50. The wavefront sensor of claim 36, further comprising an eye fixation target adapted to allow the patient to fixate without accommodation.

51. The wavefront sensor of claim 50, wherein the fixation target comprises an image of an object that appears far away to the eye.

52. The wavefront sensor of claim 36, further comprising an eye fixation target adapted to allow the patient to focus at infinity.

53. The wavefront sensor of claim 52, wherein the fixation target is adapted to support an accommodation-free status of the eye.

54. The wavefront sensor of claim 36, further comprising an eye fixation target adapted to allow the patient to focus at infinity without accommodation.

55. The wavefront sensor of claim 36, further comprising an eye fixation target adapted to allow the patient to focus at infinity with accommodation reduced.

56. The wavefront sensor of claim 36, further comprising a tuning device adapted to aid in focusing the aerial images.

57. A wavefront sensor for determining wave aberrations of an eye comprising:
  a lenslet array for receiving an image of light backscattered from a light spot on a retina of the eye and for creating aerial images of the light spot;
  a sensor adapted to receive the aerial images from the lenslet array;

a processor adapted to receive signals from the sensor corresponding to the aerial images and to determine the wave aberrations from the signals; and an adjustment camera adapted to aid in bringing into focus the aerial images from the lenslet array onto the sensor.

58. The wavefront sensor of claim 57, further comprising a pulsed laser adapted to provide light to the retina for forming the aerial images.

59. A method for focusing a wavefront sensor that creates aerial images that form centroids, comprising the steps of:

monitoring spacing of the centroids;

adjusting the focus of the sensor; and determining when the sensor is in focus by determining when the average centroid spacing equals a focused sensor centroid spacing.

60. A wavefront sensor, comprising:

a lenslet array adapted to receive an image of a light spot on a retina of an eye and for creating aerial images of the light spot;

a sensor adapted to receive the aerial images from the lenslet array;

focusing optics that adjust a focus of the sensor;

a processor adapted to receive signals from the sensor corresponding to the aerial images and to determine wave aberrations from the signals; and a focus control system that adjusts the focus of the wavefront sensor by performing a computer implemented method of:
 monitoring spacing of the aerial images;
 adjusting the focus of the sensor; and
 determining when the sensor is in focus by determining when an average spacing of the aerial images equals a focused sensor aerial image spacing.

61. The wavefront sensor of claim 60, wherein the focus control system employs the processor.

62. A method for focusing a wavefront sensor that creates aerial images that form centroids, comprising the steps of:

measuring a total wavefront error incident on the wavefront sensor;

adjusting the focus of the sensor; and determining when the sensor is in focus by determining when the total wavefront error incident on the wavefront sensor is minimized.

63. A wavefront sensor, comprising:

a lenslet array adapted to receive an image of a light spot on a retina of an eye and for creating aerial images of the light spot;

a sensor adapted to receive the aerial images from the lenslet array;

focusing optics that adjust a focus of the sensor;

a processor adapted to receive signals from the sensor corresponding to the aerial images and to determine wave aberrations from the signals; and a focus control system that adjusts the focus of the wavefront sensor by performing a computer implemented method of:
 measuring a total wavefront error incident on the wavefront sensor;
 adjusting the focus of the sensor; and
 determining when the sensor is in focus by determining when the total wavefront error incident on the wavefront sensor is minimized.

* * * * *